US012642440B2

(12) United States Patent
Li

(10) Patent No.: US 12,642,440 B2
(45) Date of Patent: Jun. 2, 2026

(54) MULTI-SENSOR DEVICE FOR CARDIOPULMONARY MANAGEMENT

(71) Applicant: Singular Medical (USA) Inc., Irvine, CA (US)

(72) Inventor: Na Li, Irvine, CA (US)

(73) Assignee: SINGULAR MEDICAL (USA) INC., Irvine, CA (US)

( * ) Notice: Subject to any disclaimer, the term of this patent is extended or adjusted under 35 U.S.C. 154(b) by 698 days.

(21) Appl. No.: 17/804,760

(22) Filed: May 31, 2022

(65) Prior Publication Data

US 2023/0380698 A1    Nov. 30, 2023

(51) Int. Cl.
A61B 5/0205        (2006.01)
A61B 5/00          (2006.01)
(Continued)

(52) U.S. Cl.
CPC .......... A61B 5/0205 (2013.01); A61B 5/6823 (2013.01); A61B 5/684 (2013.01);
(Continued)

(58) Field of Classification Search
CPC ..... A61B 5/0205; A61B 5/6823; A61B 5/684; A61B 5/7246; A61B 5/7267; A61B 5/086; A61B 5/282; A61B 5/332; A61B 7/04; A61B 5/7264; A61B 5/0245; A61B 5/36; A61B 5/366; A61B 5/0816; A61B 5/024; A61B 5/0531; A61B 5/6801; G16H 50/20; G16H 50/70; G16H 50/30; G16H 40/63; G08B 21/18; C12N 5/524
See application file for complete search history.

(56) References Cited

U.S. PATENT DOCUMENTS 10,321,877 B2 *  6/2019  Volpe ................. A61N 1/37247
2009/0076410 A1 *  3/2009  Libbus ................... G16H 40/67
                                                        600/547
(Continued)

FOREIGN PATENT DOCUMENTS

CN        110213991 A      9/2019
DE    212020000509 U1      8/2021
(Continued)

*Primary Examiner* — Jennifer Pitrak McDonald
*Assistant Examiner* — Moussa Haddad
(74) *Attorney, Agent, or Firm* — HSML P.C.

(57)                ABSTRACT

A cardiopulmonary management system includes a multi-sensor device and a controller. The multi-sensor device includes an elongated body having a first end and a second end, a first electrode disposed at the first end of the body, a second electrode disposed at the second end of the body, an electrical circuitry disposed near a middle of the body, and a sound sensor. The multi-sensor device is configured to be disposed on a skin of a subject and to measure cardiopulmonary parameters from the subject. The controller is configured to derive a score of sound change, heart rate change, thoracic impedance change, respiratory rate change, QRS wavelength change, QT interval change, electromechanical activation time change, and left ventricular systolic time change based on the measured cardiopulmonary parameters. The controller is further configured to control an operation of the system when the derived score is greater than a threshold.

20 Claims, 7 Drawing Sheets

(51) Int. Cl.

| | |
|---|---|
| *A61B 5/085* | (2006.01) |
| *A61B 5/282* | (2021.01) |
| *A61B 5/332* | (2021.01) |
| *A61B 7/04* | (2006.01) |
| *G08B 21/18* | (2006.01) |
| *G16H 50/20* | (2018.01) |

(52) U.S. Cl.
CPC .......... *A61B 5/7246* (2013.01); *A61B 5/7267* (2013.01); *G16H 50/20* (2018.01); *A61B 5/086* (2025.01); *A61B 5/282* (2021.01); *A61B 5/332* (2021.01); *A61B 7/04* (2013.01); *G08B 21/18* (2013.01)

(56) References Cited

U.S. PATENT DOCUMENTS

| | | | |
|---|---|---|---|
| 2015/0126883 A1* | 5/2015 | An | A61B 5/02028 600/513 |
| 2017/0281097 A1* | 10/2017 | Thakur | A61B 5/7275 |
| 2020/0054238 A1 | 2/2020 | Gopinathan et al. | |
| 2020/0405155 A1* | 12/2020 | Ziegler | A61B 5/746 |
| 2021/0338190 A1* | 11/2021 | Gopinathan | A61B 7/04 |
| 2022/0054848 A1* | 2/2022 | Szul | G06F 3/011 |
| 2024/0023817 A1* | 1/2024 | Vajdic | A61B 5/282 |
| 2024/0215896 A1* | 7/2024 | Vajdic | A61B 5/327 |

FOREIGN PATENT DOCUMENTS

| | | | | |
|---|---|---|---|---|
| EP | 3310251 B1 | 8/2019 | | |
| WO | WO-2020148280 A2 * | 7/2020 | | A61B 5/086 |

* cited by examiner

MULTI-SENSOR DEVICE FOR CARDIOPULMONARY MANAGEMENT

FIELD

This disclosure relates generally to systems and methods for cardiopulmonary management. More specifically, the disclosure relates to systems and methods of managing cardiopulmonary conditions such as heart failure or the like using sensed or measured data from a multi-sensor device, providing early alarm(s) for worsening cardiopulmonary conditions, and/or predicting parameters indicating cardiopulmonary conditions.

BACKGROUND

Cardiopulmonary management typically refers to managing cardiopulmonary conditions. Cardiopulmonary conditions may refer to the conditions of the heart ("cardio-") and/or lungs ("-pulmonary") including cardiopulmonary diseases and/or normal and healthy heart and/or lungs. Cardiopulmonary diseases typically refer to a range of disorders that affect the heart and/or lungs such as cardiovascular diseases, chronic obstructive pulmonary disorder, or the like. Cardiovascular diseases may include heart attack, stroke, heart failure, arrhythmia, heart valve complications, etc. Heart failure may be referred to as a chronic, progressive condition in which the heart muscle is unable to pump enough blood to meet the body's needs for blood and/or oxygen.

SUMMARY

This disclosure relates generally to systems and methods for cardiopulmonary management. More specifically, the disclosure relates to systems and methods of managing cardiopulmonary conditions such as heart failure or the like using sensed or measured data from a multi-sensor device, providing early alarm(s) for worsening cardiopulmonary conditions, and/or predicting parameters indicating cardiopulmonary conditions.

In an embodiment, a cardiopulmonary management system is provided. The system includes a multi-sensor device and a controller. The multi-sensor device includes an elongated body having a first end and a second end, a first electrode disposed at the first end of the body, a second electrode disposed at the second end of the body, an electrical circuitry disposed near a middle of the body, and a sound sensor. The multi-sensor device is configured to be disposed on a skin of a subject and to measure cardiopulmonary parameters from the subject. The controller is configured to derive a score of sound change, heart rate change, thoracic impedance change, respiratory rate change, QRS wavelength change, QT interval change, electromechanical activation time change, and left ventricular systolic time change based on the measured cardiopulmonary parameters. The controller is further configured to control an operation of the system when the derived score is greater than a threshold.

In an embodiment, a method of controlling an operation of a cardiopulmonary management system is provided. The system includes a multi-sensor device and a controller. The multi-sensor device includes an elongated body having a first end and a second end, a first electrode disposed at the first end of the body, a second electrode disposed at the second end of the body, an electrical circuitry disposed near a middle of the body, and a sound sensor. The method includes positioning the multi-sensor device on a skin of a subject, and sensing cardiopulmonary parameters from the subject. The method also includes deriving a score of sound change, heart rate change, thoracic impedance change, respiratory rate change, QRS wavelength change, QT interval change, electromechanical activation time change, and left ventricular systolic time change based on the measured cardiopulmonary parameters. The method further includes controlling the operation of the system when the derived score is greater than a threshold.

In an embodiment, a method of predicting cardiopulmonary parameters is provided. The method includes measuring a first set of cardiopulmonary parameters, measuring a second set of cardiopulmonary parameters, determining a correlation between the first set of cardiopulmonary parameters and the second set of cardiopulmonary parameters using machine learning, positioning a multi-sensor device on a skin of a subject, sensing the first set of cardiopulmonary parameters from the subject by the multi-sensor device, and predicting the second set of cardiopulmonary parameters for the subject based on the determined correlation using machine learning.

In an embodiment, a method of positioning a multi-sensor device is provided. The multi-sensor device includes an elongated body having a first end and a second end, a first electrode disposed at the first end of the body, a second electrode disposed at the second end of the body, and a sound sensor. The method includes capturing, by a camera, an image of a subject. The method also includes displaying the captured image on a display device. The method further includes indicating a first location, a second location, and a third location on the displayed image. Also the method includes positioning and securing the first end of the elongated body of the multi-sensor device at a first position corresponding to the first location on a skin of the subject, positioning and securing the second end of the elongated body of the multi-sensor device at a second position corresponding to the second location on the skin of the subject, and positioning and securing the sound sensor at a third position corresponding to the third location on the skin of the subject.

It will be appreciated that acute heart failure may result in irreversible heart muscle damage. Early alarm on a subject's health condition can enable the physician to adjust the subject's treatment and medicine in time, reducing the heart muscle damage and the subject's readmission to hospital. Because of various physical change(s) in different subject during an early stage of worsening health condition, it may be difficult for a single sensor to detect the worsening condition timely.

Embodiments disclosed herein can provide early alarm(s) on worsening health conditions such as heart failure, pulmonary effusion or the level of thoracic fluid content, instable heart condition, or the like, with a non-intrusive, atraumatic, and easy to use cardiopulmonary management system. Embodiments disclosed herein can also provide a multi-sensor device that monitors the cardiac and pulmonary conditions by different sensors and sends the early warning of the changes indicating worsening health conditions.

Embodiments disclosed herein can also provide an external multi-sensor device for monitoring health conditions of the heart or the lung(s). The device can be used to monitor the change of the health conditions over time. The device can be used continuously over a period of time, or continuously over a period of time at a predetermined interval (e.g., a period of time every day, a period of time every week, etc.).

Other features and aspects will become apparent by consideration of the following detailed description and accompanying drawings.

BRIEF DESCRIPTION OF THE DRAWINGS

References are made to the accompanying drawings that form a part of this disclosure and which illustrate the embodiments in which systems and methods described in this specification can be practiced.

Figure 1:
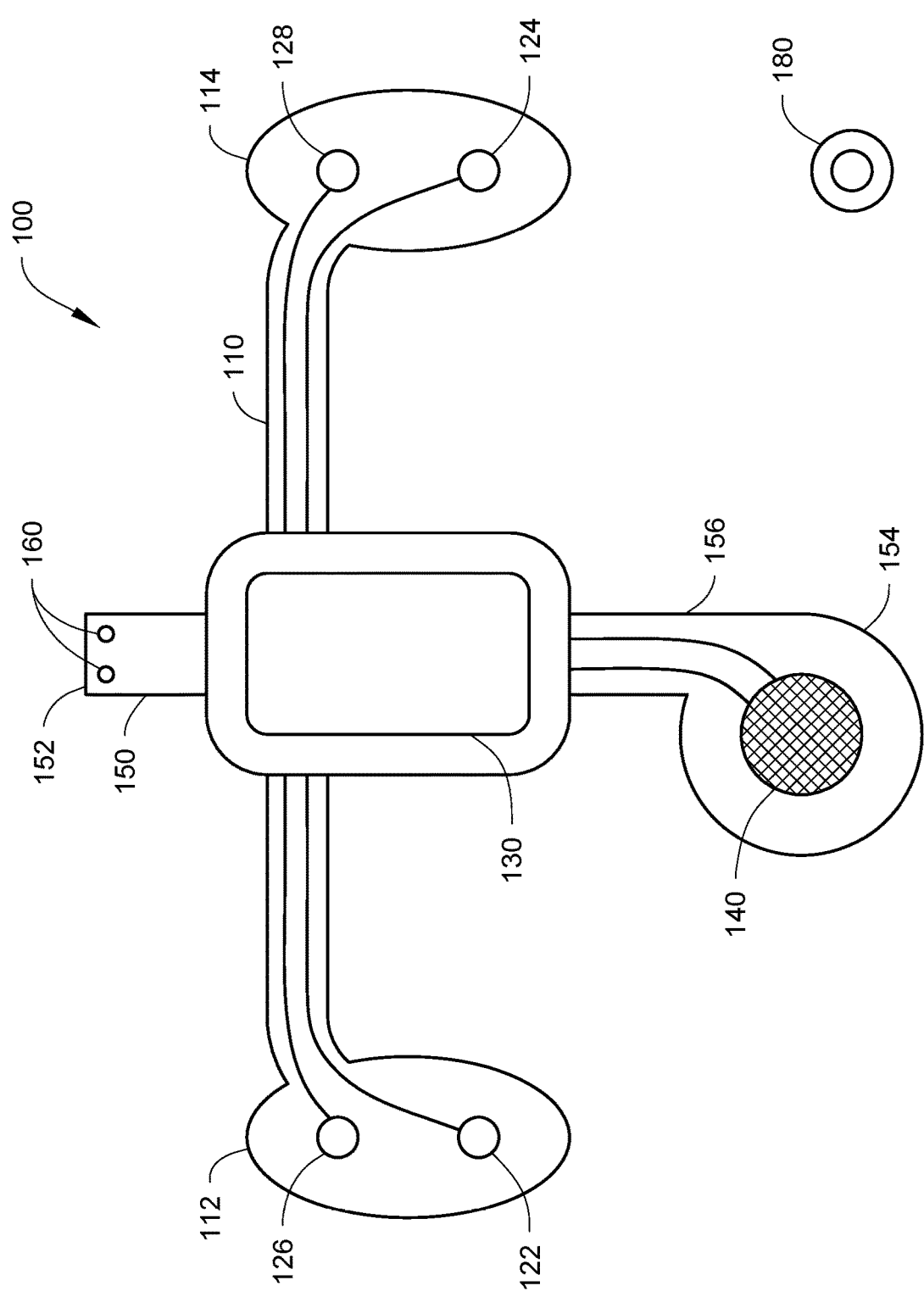
FIG. 1 is a back view of a multi-sensor device, according to an embodiment.

Particular embodiments of the present disclosure are described herein with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent like elements that may perform the same, similar, or equivalent functions.

DETAILED DESCRIPTION

This disclosure relates generally to systems and methods for cardiopulmonary management. More specifically, the disclosure relates to systems and methods of managing cardiopulmonary conditions such as heart failure or the like using sensed or measured data from a multi-sensor device, providing early alarm(s) for worsening cardiopulmonary conditions, and/or predicting parameters indicating cardiopulmonary conditions.

As defined herein, the phrase "electrocardiogram" may refer to a recording of the heart's electrical activity, electrical signals, or electrical conduction, which can be a graph of voltage versus time of the electrical activity of the heart, by using e.g., electrodes placed on the skin or the like. An electrocardiogram may include a P wave, a QRS complex and a T wave. The P wave indicates atrial depolarization. The QRS complex includes a Q wave, an R wave, and an S wave, and represents ventricular depolarization. The T wave comes after the QRS complex and indicates ventricular repolarization.

As defined herein, the phrase "thoracic impedance" may refer to the impedance (i.e., the hindrance to the flow of the current carried by ions) along a measurement path (or a vector, e.g., from one electrode to another electrode). As defined herein, the phrase "transthoracic impedance" may refer to the thoracic impedance across the chest (e.g., spanning the whole chest or the pair of lungs). That is, the transthoracic impedance is the thoracic impedance when the measurement path of the thoracic impedance spans the entire chest. Transthoracic impedance can be affected by factors including chest size, distance between the electrodes (to measure or sense the transthoracic impedance), electrode size, and/or the interface between the electrodes and the chest wall. It will be appreciated that transthoracic impedance can be related to the total amount of intrathoracic fluid.

As defined herein, the phrase "heart sounds" may refer to the sounds created from blood flowing through the heart chambers as the cardiac valves open and close during the cardiac cycle. A normal heartbeat has two sounds: the first heart sound (S1) and the second heart sound (S2). S1 results from the closing of the mitral and tricuspid valves. S2 is produced by the closure of the aortic and pulmonic valves. If there are problems in the heart, there may be additional or abnormal sounds. The third heart sound (S3) and the fourth heart sound (S4) are two abnormal heart sound components which are proved to be indicators of heart failure during diastolic period and/or of impairment of the heart function. S1 and S2 are high-pitched (high frequency) sounds and S3 and S4 are low-pitched (low frequency) sounds. If there is an S3, such S3 typically occurs just after S2 (e.g., about 120 milliseconds to 180 milliseconds after S2) when the mitral valve opens, allowing passive filling of the left ventricle (LV). The S3 sound is produced by the large amount of blood striking a very compliant LV. If the LV is not overly compliant, as is in most adults, a S3 may not be loud enough to be sensed/measured/auscultated. S3 is often a sign of systolic congestive heart failure because if there is S3, the myocardium is usually overly compliant, resulting in a dilated LV. S3 can be sensed best at the cardiac apex.

As defined herein, the phrase "morphology" or "waveform" may refer to the shape, amplitude, and/or duration of the potentials which are the electrical signals in an electrocardiogram, in a thoracic impedance recording, in sounds recording (e.g., heart sounds, lung sounds, etc.), or the like, which are recorded or measured over a period of time.

Some embodiments of the present application are described in detail with reference to the accompanying drawings so that the advantages and features of the present application can be more readily understood by those skilled in the art. The terms "near", "far", "top", "bottom", "left", "right", and the like described in the present application are defined according to the typical observation angle of a person skilled in the art and for the convenience of the description. These terms are not limited to specific directions.

Processes described herein may include one or more operations, actions, or functions depicted by one or more blocks. It will also be appreciated that although illustrated as discrete blocks, the operations, actions, or functions described as being in various blocks may be divided into additional blocks, combined into fewer blocks, or eliminated, depending on the desired implementation. Any features described in one embodiment may be combined with or incorporated/used into the other embodiment, and vice versa. The scope of the disclosure should be determined by the appended claims and their legal equivalents, rather than by the examples given herein. For example, the steps recited in any method claims may be executed in any order and are not limited to the order presented in the claims. Moreover, no element is essential to the practice of the disclosure unless specifically described herein as "critical" or "essential."

It will be appreciated that unless otherwise specified, data sensed or measured can be partially processed or fully processed to derive other data from the sensed or measured data.

FIG. 1 is a back view of a multi-sensor device 100, according to an embodiment. The multi-sensor device 100 includes an elongated body 110. The body 110 extends in a substantially horizontal direction and has a first end 112 and a second end 114. A first electrode 122 is disposed at the first end 112 of the body 110. A second electrode 124 is disposed at the second end 114 of the body 110. An electrical circuitry 130 (e.g., a flexible circuit board) is disposed near a middle of the body 110. The multi-sensor device 100 further includes a sound sensor 140.

In an embodiment, the electrical circuitry 130 includes a controller (not shown). The controller can include a processor, memory (or storage), and/or communication ports to communicate with e.g., other components of the multi-sensor device (100, 102 of FIG. 2), specially programmed computer, portable (or mobile) electronic device such as a smartphone, a tablet, a personal data assistant (PDA), a personal media player device, a wireless web-watch device, a personal headset device, an application specific device, a hybrid device that include any of the above functions, a personal computer including both laptop computer and non-laptop computer configurations, a server, cloud, or the like. The controller can communicate with other components using any suitable communications including wired and/or wireless (e.g., Bluetooth®, or the like), analog and/or digital communications. The controller can obtain data sensed or measured by the sensors or electrodes of the multi-sensor device (100, 102 of FIG. 2) and control the settings of the sensors, electrodes, and/or other components of the multi-sensor device (100, 102 of FIG. 2).

In an embodiment, the electrical circuitry 130 includes a power source (e.g., a battery or the like, not shown) to power the components of the multi-sensor device. The battery can be rechargeable through e.g., the contact charging point(s) 160 connecting to a charging station/dock (not shown).

In an embodiment, a length of the body 110 can be a width of a chest of a subject (e.g., 200 of FIG. 3) extending from e.g., one armpit to another armpit of the subject. In an embodiment, the length of the body 110 can be extendable or retractable. The body 110 can be made of flexible silicone or any other suitable material. In an embodiment, a third electrode 126 can be disposed at the first end 112 of the body 110, and a fourth electrode 128 can be disposed at the second end 114 of the body 110. In an embodiment, the first end 112 and/or the second end 114 can have an ellipse or any suitable shape.

In an embodiment, the pair of electrodes (122, 124) can be aligned with each other in a horizontal or substantially horizontal direction. The pair of electrodes (126, 128) can be aligned with each other in a horizontal or substantially horizontal direction. The electrode 122 and the electrode 126 can be aligned with each other in a vertical or substantially vertical direction. The electrode 124 and the electrode 128 can be aligned with each other in a vertical or substantially vertical direction. A distance between the electrode 122 and the electrode 126 can range from at or about two centimeters to at or about four centimeters. A distance between the electrode 124 and the electrode 128 can range from at or about two centimeters to at or about four centimeters. The distance and alignment(s) can be critical for e.g., conducting measurements to get most reliable and/or stable results.

As shown in FIG. 1, the electrodes (122, 124, 126, and 128) connect to the electrical circuitry 130 via corresponding wires, respectively. In another embodiment, the electrodes (122, 124, 126, and 128) can wirelessly connect to the electrical circuitry 130.

In an embodiment, the multi-sensor device 100 can include an extension 150 extending cross a middle of the elongated body 110 and integral to the body 110. The extension 150 can be made of silicone (e.g., pure silicone) or any other suitable material. The extension 150 extends substantially vertically and has a first end 152 and a second end 154 extending horizontally from other parts of the extension 150. The sound sensor 140 is disposed at or near the second end 154 of the extension 150. Contact charging point(s) 160 can be disposed at the first end 152 of the extension 150. In an embodiment, the extension 150 can have a trunk 156 connected to the second end 154. The trunk 156 can have a fixed curve or be extendable/retractable so that the sound sensor 140 can be disposed near the cardiac apex on the skin of the subject or be extended to the back of the subject near a lung of the subject. It will be appreciated that in some embodiments, the components of the multi-sensor device 100 can be disposed at any suitable locations on the multi-sensor device 100.

In an embodiment, the multi-sensor device 100 can include pad(s) 180. Each pad 180 can be disposed between the respective electrodes (122, 124, 126, and 128) and the skin of the subject. The pad(s) 180 can be self-adhesive pads (e.g., with a conductive gel in the center) or sticky patches to secure the respective electrodes (122, 124, 126, and 128) to the skin. In another embodiment, the pad(s) 180 can be optional.

In an embodiment, the sound sensor 140 can be acoustic sensor, acoustic-pressure sensor, or the like, configured to sense/measure/detect sounds (e.g., heart sounds when the sound sensor 140 is disposed near the cardiac apex, lung sounds when the sound sensor 140 is disposed at the back of the subject near a lung, or the like) and/or bio-acoustic signals from the subject in real-time or over a period of time. The data sensed by the sound sensor 140 can be communicated (wirelessly or via wire) to e.g., the controller of the multi-sensor device 100 or any other suitable controllers (e.g., controller(s) of portable/mobile electronic device(s), personal computer(s), server(s), or controller(s) in the cloud, or the like).

As shown in FIG. 1, the sound sensor 140 connects to the electrical circuitry 130 via wire(s). In another embodiment, the sound sensor 140 can wirelessly connect to the electrical circuitry 130.

In an embodiment, the electrodes (122, 124, 126, and 128) can be configured to measure the thoracic or transthoracic impedance and/or the electrocardiogram of the heart. In an embodiment, each of the electrodes (122, 124, 126, and 128) can include a wet electrode sensor, a dry electrode sensor, a textile-based sensor, a knitted integrated sensor, a planar fashionable circuit board, or the like. For example, when the electrodes (122, 124, 126, and 128) include wet sensor(s), they typically need the use of a conductive gel to increase conductivity between the skin and the electrodes. The data sensed or measured by the electrodes (122, 124, 126, and 128) can be communicated (wirelessly or via wire) to e.g., the controller of the multi-sensor device 100 or any other suitable controllers (e.g., controller(s) of portable/mobile electronic device(s), personal computer(s), server(s), or controller(s) in the cloud, or the like).

In an embodiment, the controller of the electrical circuitry 130 can be configured to control the operation of, to configure or set up the operational parameters of, and/or to communicate with other components of the multi-sensor device 100 (such as the sound sensor 140, the electrodes (122, 124, 126, and 128), or the like), to e.g., obtain the sensed or measured data from the sensor(s) and/or electrode(s), to control the electrode(s) to apply an electrical force (e.g., a current or a voltage) to the subject, or the like.

In an embodiment, the multi-sensor device can include accelerometer(s), temperature sensor(s), pressure sensor, weight sensor, oximeter, or the like. Such sensors can sense or measure cardiopulmonary parameters (e.g., activity, body temperature, blood pressure, body weight, blood oxygen saturation, or the like) from the subject. The controller can obtain such data and use the data in deriving, predicting, and/or analyzing other cardiopulmonary parameters. Embodiment disclosed herein can provide a fixed cross-structure to facilitate the ease of locating the desired location, e.g., by aligning an upper end of the extension 150 with the collarbone so that the locations of the other parts of the multi-sensor device can be determined. Embodiment disclosed herein can also measure the thoracic impedance of the entire pair of lungs, and thus can measure stronger signals and can get more accurate measurements compared with measuring partial lung(s).

Figure 2:
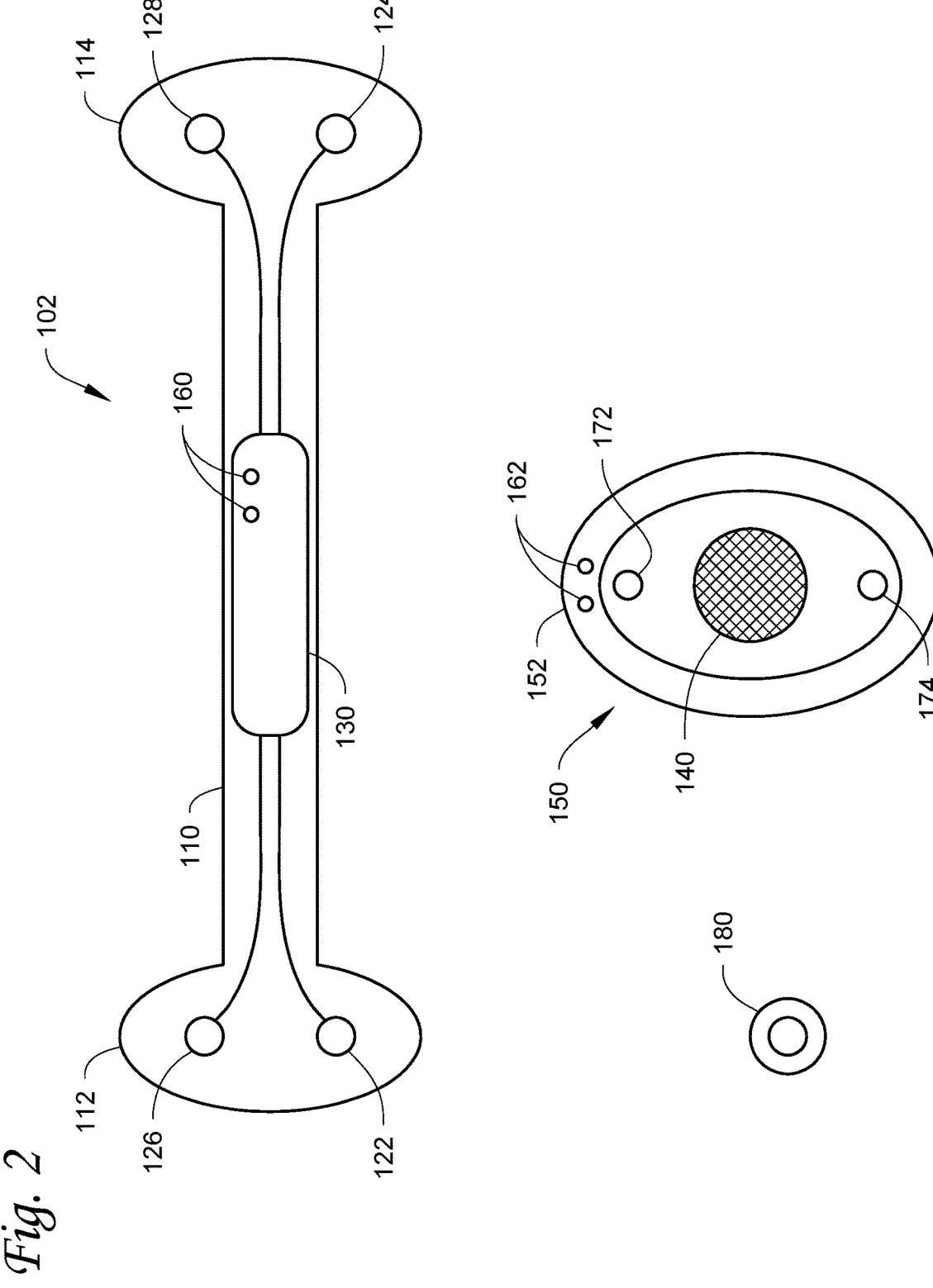
FIG. 2 is a back view of a multi-sensor device, according to another embodiment.

FIG. 2 is a back view of a multi-sensor device 102, according to another embodiment. It will be appreciated that the multi-sensor device 102 can be the same as or similar to the multi-sensor device 100 of FIG. 2, unless otherwise specified.

As shown in FIG. 2, the multi-sensor device 102 can include an extension 150 separate from the body 110 of the multi-sensor device 102. The sound sensor 140 can be disposed on the extension 150. The extension 150 has a first end 152 and a second end 154. A first extension electrode 172 is disposed at or near the first end 152 of the extension 150. A second extension electrode 174 is disposed at or near the second end 154 of the extension 150. The sound sensor 140 is disposed at or near a middle of the extension 150. The extension 150 can include contact charging point(s) 162 disposed at or near the first end 152 of the extension 150. It will be appreciated that in some embodiments, the components of the multi-sensor device 102 can be disposed at any suitable locations. In an embodiment, a distance between the first extension electrode 172 and the second extension electrode 174 ranges from at or about five centimeters to at or about 10 centimeters. In an embodiment, an angle (e.g., when the extension 150 is placed in position on the skin of the subject) from the line (formed by connecting the first extension electrode 172 and the second extension electrode 174) to the horizontal direction is at or about 60 degrees or at or about 120 degrees or any suitable degrees. The distance and angle can be critical for e.g., conducting measurements to get most reliable and/or stable results.

In an embodiment, the extension 150 can include a power source (e.g., a battery or the like, not shown) to power the components of the extension 150. The battery can be rechargeable through e.g., the contact charging point(s) 162 (that is disposed at or near the first end 152 of the extension 150) connecting to a charging station/dock (not shown). On the body 110, contact charging point(s) 160 can be disposed on the electrical circuitry 130.

In an embodiment, the structure and/or functions of the electrode(s) 172 and 174 can be the same as the electrodes (122, 124, 126, and 128). In another embodiment, the structure and/or functions of the electrode(s) 172 and 174 can be different from the electrodes (122, 124, 126, and 128).

In an embodiment, the controller of the electrical circuitry 130 can be configured to control the operation of, to configure or set up the operational parameters of, and/or to communicate with other components of the multi-sensor device 102 (such as the sound sensor 140, the electrodes (122, 124, 126, 128, 172, and 174), or the like), to e.g., obtain the sensed or measured data from the sensor(s) and/or electrode(s), to control the electrode(s) to apply an electrical force (e.g., a current or a voltage) to the subject, or the like.

In another embodiment, instead of communicating with the controller of the electrical circuitry 130, the components on the extension 150 (or the components of the multi-sensor device 102) may communicate with any other suitable controller(s) (e.g., controller(s) of portable/mobile electronic device(s), personal computer(s), server(s), or controller(s) in the cloud, or the like) to send over the sensed or measured data. In another embodiment, the body 110 and/or the extension 150 can be made in a form of a patch or a pad.

Embodiment disclosed herein can separate the measurements of the thoracic impedance from the electrocardiogram and the sound, to facilitate the locating of the desired locations for subjects with different body shape. Embodiment disclosed herein can also measure the thoracic impedance of the entire pair of lungs, and thus can measure stronger signals and can get more accurate measurements compared with measuring partial lung(s).

Figure 4:
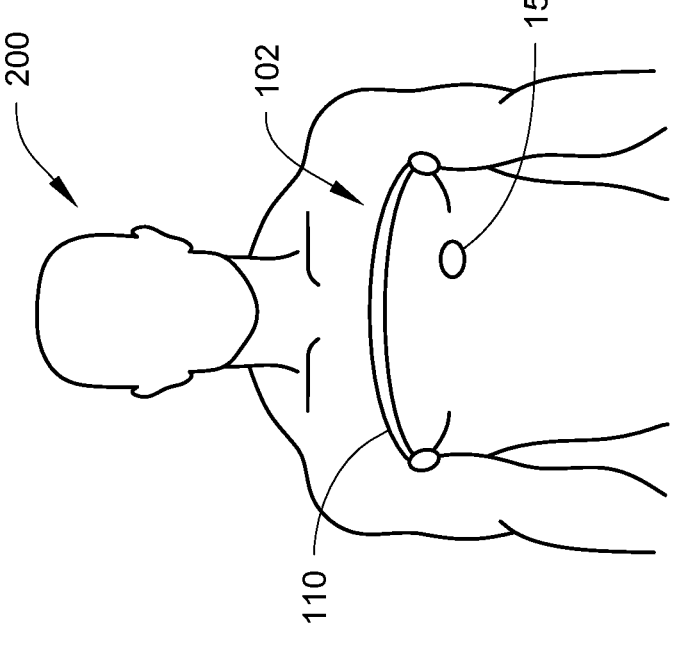
FIG. 4 is a schematic view of the multi-sensor device of FIG. 2 disposed on a skin a subject, according to an embodiment.
Figure 3:
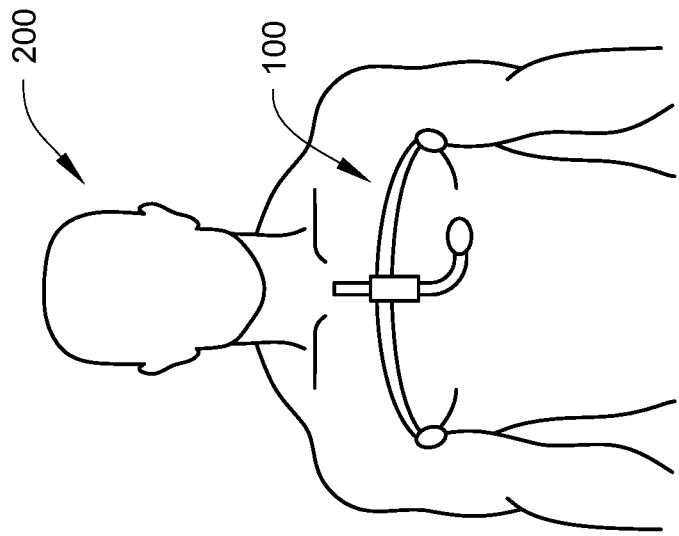
FIG. 3 is a schematic view of the multi-sensor device of FIG. 1 disposed on a skin a subject, according to an embodiment.

FIG. 3 is a schematic view of the multi-sensor device 100 of FIG. 1 disposed on a skin a subject 200, according to an embodiment. FIG. 4 is a schematic view of the multi-sensor device 102 of FIG. 2 disposed on a skin a subject 200, according to an embodiment. The elongated body 110 of the multi-sensor device (100, 102) spans across a chest of the subject, and the sound sensor 140 is disposed on the skin of the subject near the cardiac apex. The subject 200 can be e.g., a person using or testing the multi-sensor device.

Figure 5:
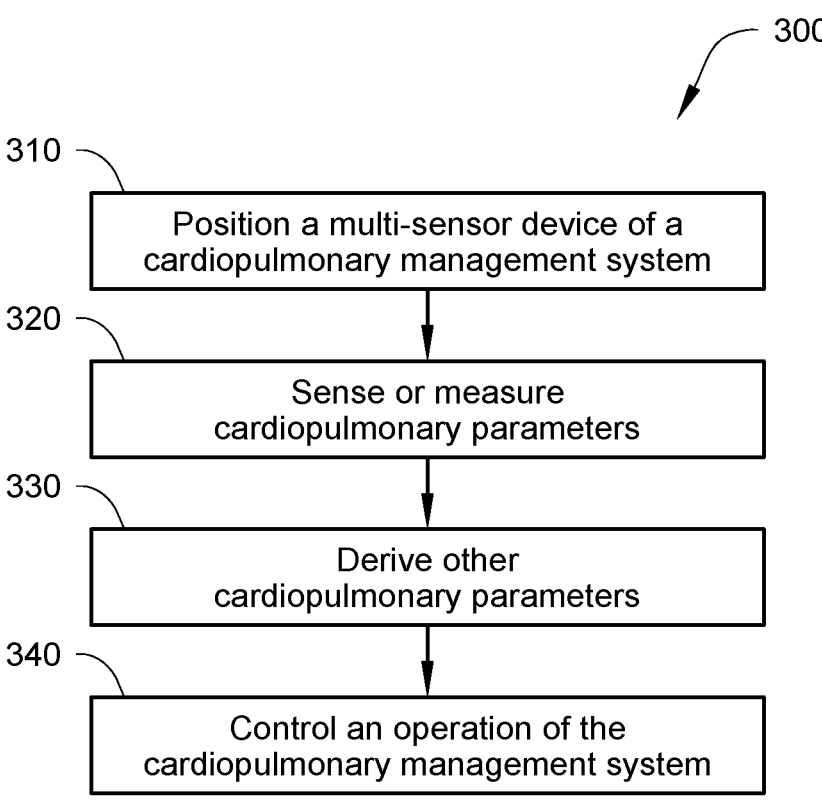
FIG. 5 is a flow chart illustrating a method of controlling an operation of a cardiopulmonary management system, according to an embodiment.

FIG. 5 is a flow chart illustrating a method 300 of controlling an operation of a cardiopulmonary management system, according to an embodiment. The cardiopulmonary management system includes a multi-sensor device (100 of FIG. 1 or 102 of FIG. 2). The cardiopulmonary management system further includes a controller. The controller can be the controller of the multi-sensor device, other controller (the controller of a portable/mobile electronic device, a specially programmed personal computer, a server, or controller(s) in the cloud, or the like), or the combination thereof. It will be appreciated that the method steps disclosed herein can be conducted by the controller, unless otherwise specified.

The controller can include a processor, memory, and/or communication ports to communicate with e.g., other components of the cardiopulmonary management system, using any suitable communications including wired and/or wireless, analog and/or digital communications. The controller can obtain data sensed or measured by the sensors and/or electrodes and control the settings of the sensors and/or electrodes and/or other components of the cardiopulmonary management system.

It will also be appreciated that the method 300 can include one or more operations, actions, or functions depicted by one or more blocks. Although illustrated as discrete blocks, various blocks may be divided into additional blocks, combined into fewer blocks, or eliminated, depending on the desired implementation. The method 300 can be in a form of e.g., an application (APP) for a mobile device, an algorithm, or the like.

The method 300 begins at 310. At 310, a user can position the multi-sensor device at the desired location/position on a skin of a subject (see 200 of FIG. 3). The method step 310 is described in more detail in FIGS. 6A-6C.

The method 300 proceeds to 320. At 320, the sensor(s) and/or electrode(s) of the multi-sensor device are configured to sense or measure cardiopulmonary parameters from the subject. Before the sensor(s) and/or electrode(s) sensing or measuring the cardiopulmonary parameters, the controller can be configured to e.g., initialize the sensor(s) and/or electrode(s) by. e.g., configuring or setting up operational parameters (amplitude and/or duration of the voltage and/or current applied, sensing or sampling parameters such as sampling frequency, sampling resolutions, sampling intervals, sampling durations, or the like) of the sensor(s) and/or electrode(s). After the sensor(s) and/or electrode(s) sensing or measuring the cardiopulmonary parameters, the controller can be configured to obtain the parameters sensed or measured by the sensors and/or electrodes.

The cardiopulmonary parameters to be measured can include thoracic or transthoracic impedance, electrocardiogram of the heart, and/or sounds (e.g., heart sounds when the sound sensor being disposed on the skin of the subject near the cardiac apex, or lung sounds when the sound sensor being disposed on the skin at the back of the subject near a lung, or the like). In an embodiment, the measured cardiopulmonary parameters can be measured and recorded in the form of waveform or morphology.

In operation, the sound sensor can be configured to sense the sounds (including those that might not be able to obtained or measured via a stethoscope) in real-time and/or over a period of time.

In operation, the electrode(s) can be configured to sense or measure the thoracic impedance and/or the electrocardiogram. In an embodiment, a single pair of electrodes (e.g., 122 and 124, or 126 and 128) can be configured to sense or measure both the thoracic impedance and the electrocardiogram. In another embodiment, one pair of electrodes (e.g., 122 and 124, or 126 and 128) can be configured to sense or measure the thoracic impedance and another pair of electrodes (e.g., 126 and 128, or 122 and 124) can be configured to sense or measure the electrocardiogram, or vice versa. In yet another embodiment, one pair of electrodes (e.g., 122 and 124, or 126 and 128) can be configured to sense or measure the thoracic impedance and both pair of electrodes (e.g., 122, 124, 126, and 128) can be configured to sense or measure the electrocardiogram. In yet another embodiment, one pair of electrodes (e.g., 122 and 124, or 126 and 128) can be configured to sense or measure the electrocardiogram and both pair of electrodes (e.g., 122, 124, 126, and 128) can be configured to sense or measure the thoracic impedance. In yet another embodiment, one pair of electrodes (e.g., 122 and 124, or 126 and 128) can be configured to sense or measure the thoracic impedance and one of more pairs of electrodes (e.g., 122 and 124, 126 and 128, and/or 172 and 174) can be configured to sense or measure the electrocardiogram. In yet another embodiment, one pair of electrodes (e.g., 172 and 174) can be configured to sense or measure the electrocardiogram and one of more pairs of electrodes (e.g., 122 and 124, 126 and 128, and/or 172 and 174) can be configured to sense or measure the thoracic impedance.

When a pair of electrodes is configured to sense or measure the thoracic impedance, one electrode of the pair is configured as a force electrode and the other electrode of the pair is configured as a sense electrode. The force electrode is configured to apply an electrical force (such as a current or a voltage) to the subject and the sense electrode is configured to sense signals or changes caused by the applied electrical force. The changes may include changes in a voltage drop between the electrodes of the pair, changes in current flow between the electrodes of the pair, changes in conductance between the electrodes of the pair, or some combination thereof.

For example, the electrical circuitry 130 can be configured or controlled (by the controller) to apply (e.g., via the wire connecting to the force electrode or the like), a suitable current (at a suitable voltage at the force electrode) between the pair of electrodes using electrical energy from the power source. The sense electrode can be configured to sense or measure the potential difference between the force electrode and the sense electrode (e.g., by measuring the voltage at the sense electrode, which can be compared with the voltage applied at the force electrode, or the like). Since voltage and current are related to impedance ($V = Z \times I$), to measure impedance Z, a known current I can be applied, and the subsequent voltage drop V can be measured or sensed, and Z can be determined using the known current I and measured change in voltage V. As such, the data required for measuring the thoracic impedance (impedance between the force electrode and the sense electrode of the pair) can be sensed or measured, and the thoracic impedance can be determined (e.g., by the controller or the like) based on the measured data (current, voltage, and/or voltage drop, or the like). In operation, the pair of electrode can be configured to sense or measure the thoracic impedance (or sense or measure data for determining the thoracic impedance) in real-time and/or over a period of time.

When a pair of electrodes is configured to sense or measure the electrocardiogram, electrical activity or electrical potential or voltage (of the heart) between one electrode of the pair and the other electrode of the pair can be sensed or measured, and an electrocardiogram can be determined and/or recorded (e.g., by the controller or the like). In operation, the pair of electrode can be configured to sense or measure the electrocardiogram (or sense or measure data for determining the electrocardiogram) in real-time and/or over a period of time. The electrocardiogram can be determined (e.g., by the controller or the like) as a form of waveform.

It will be appreciated that when a pair of electrodes is used to sense or measure two types of measurements, i.e., both the thoracic impedance (or data for determining the thoracic impedance) and the electrocardiogram (or data for determining the electrocardiogram), multiplex, time-sharing, or time-splitting technologies may be used to sense or measure the thoracic impedance and the electrocardiogram simultaneously or alternately at different time slots (e.g., one measurement type after the other measurement type, or one measurement type for a period of time and then the other measurement type for a period of time, or the like).

The method 300 proceeds to 330. At 330, the controller is configured to derive other cardiopulmonary parameters from the measured cardiopulmonary parameters (thoracic impedance, electrocardiogram, and/or sounds).

In an embodiment, the cardiopulmonary parameters to be derived can include S1, S2, and/or S3 derived from the measured heart sounds, and/or sound(s) derived from the measured lung sounds. Amplitude, duration, intervals (among S1, S2, and/or S3), and/or intensity (e.g., loudness or the like) of S1, S2, and/or S3 can be also derived. The cardiopulmonary parameters to be derived can also include one or more of the heart rate (derived from the measured electrocardiogram or the measured heart sounds), the transthoracic impedance (same as or derived from the measured thoracic impedance), the respiratory rate (derived from the measured electrocardiogram or the measured or recorded waveform of the thoracic impedance), the QRS wavelength or QRS duration (derived from the measured electrocardiogram), the QT interval (derived from the measured electrocardiogram), the electromechanical activation time (the time/interval measured from the beginning of the QRS complex (or from the beginning of electrical activation of left ventricle or the onset of the Q wave) to the peak of S1 or S1 wave (or to the onset of the S1 or the onset of the mitral valve closure), derived from the measured electrocardiogram and the measured heart sounds), the left ventricular systolic time (the time or interval between S1 and S2, derived from the measured heart sounds), or the like. In an embodiment, the cardiopulmonary parameters to be derived can further include tidal volume (derived from the measured thoracic impedance) and/or indication of rapid shallow breathing (a ratio of the derived respiratory rate to the derived tidal volume).

In an embodiment, a change of the sound (e.g., a change of a ratio of an intensity of S3 to an intensity S1, the ratio can be represented by "S3/S1" when S3 is detected (e.g., sensed or measured)) can be determined based on the derived sounds. For example, a heart sound baseline can be measured or determined for the subject as an average S3/S1 during a period of time when the subject is taking reasonable medication and/or is in a stable health condition. A change of the heart sound (S3/S1) for the subject (e.g., a change of an average S3/S1 over a period of time) can be determined when S3 is detected (e.g., sensed or measured) and when the derived heart sound S3/S1 is compared with the heart sound baseline. In an embodiment, every at or about 5% increase of S3/S1 (from the heart sound baseline) for the derived S3/S1 can be considered as one point. It will be appreciated that using S3/S1 instead of individual S3 and/or S1 can provide more reliable or stable data since the absolute value of S3 and/or S1 may be subject to noise and/or depending on the amplitude or strength or intensity of the sensed signal.

In an embodiment, a change of the heart rate can be determined based on the derived heart rate. For example, a heart rate baseline can be measured or determined for the subject as an average heart rate during a period of time when the subject is taking reasonable medication and/or is in a stable health condition. A change of the heart rate (e.g., a change of an average heart rate over a period of time) can be determined when the derived heart rate is compared with the heart rate baseline. In an embodiment, every at or about 10 beats per minute increase (from the heart rate baseline) for the derived heart rate can be considered as one point.

In an embodiment, a change of the thoracic (or transthoracic) impedance can be determined based on the derived/measured thoracic impedance. For example, a thoracic impedance baseline can be measured or determined for the subject as an average thoracic impedance during a period of time when the subject is taking reasonable medication and/or is in a stable health condition, or during a period of time when the subject uses the multi-sensor device for the first time. A change of the thoracic impedance (e.g., a change of an average thoracic impedance over a period of time) can be determined when the derived/measured thoracic impedance is compared with the thoracic impedance baseline. In an embodiment, every at or about 5% decrease (from the thoracic impedance baseline) for the derived/measured thoracic impedance can be considered as one point.

In an embodiment, a change of the respiratory rate can be determined based on the derived respiratory rate. For example, a respiratory rate baseline can be measured or determined for the subject as an average respiratory rate during a period of time when the subject is taking reasonable medication and/or is in a stable health condition. A change of the respiratory rate (e.g., a change of an average respiratory rate over a period of time) can be determined when the derived respiratory rate is compared with the respiratory rate baseline. In an embodiment, every at or about 10% increase (from the respiratory rate baseline) for the derived respiratory rate can be considered as one point.

In an embodiment, a change of the QRS wavelength (or duration) can be determined based on the derived QRS wavelength. For example, a QRS wavelength baseline can be measured or determined for the subject as an average QRS wavelength during a period of time when the subject is taking reasonable medication and/or is in a stable health condition. A change of the QRS wavelength (e.g., a change of an average QRS wavelength over a period of time) can be determined when the derived QRS wavelength is compared with the QRS wavelength baseline. In an embodiment, every at or about 5% increase (from the QRS wavelength baseline) for the derived QRS wavelength can be considered as one point.

In an embodiment, a change of the QT interval can be determined based on the derived QT interval. For example, a QT interval baseline can be measured or determined for the subject as an average QT interval during a period of time when the subject is taking reasonable medication and/or is in a stable health condition. A change of the QT interval (e.g., a change of an average QT interval over a period of time) can be determined when the derived QT interval is compared with the QT interval baseline. In an embodiment, every at or about 5% increase (from the QT interval baseline) for the derived QT interval can be considered as one point.

In an embodiment, a change of the electromechanical activation time (EMAT) can be determined based on the derived EMAT. For example, an EMAT baseline can be measured or determined for the subject as an average EMAT during a period of time when the subject is taking reasonable medication and/or is in a stable health condition. A change of the EMAT (e.g., a change of an average EMAT over a period of time) can be determined when the derived EMAT is compared with the EMAT baseline. In an embodiment, every at or about 5% increase (from the EMAT baseline) for the derived EMAT can be considered as one point.

In an embodiment, a change of the left ventricular systolic time (LVST) can be determined based on the derived LVST. For example, an LVST baseline can be measured or determined for the subject as an average LVST during a period of time when the subject is taking reasonable medication and/or is in a stable health condition. A change of the LVST (e.g., a change of an average LVST over a period of time) can be determined when the derived LVST is compared with the LVST baseline. In an embodiment, every at or about 5% increase (from the LVST baseline) for the derived LVST can be considered as one point.

It will be appreciated that each point can indicate a degree of worsening of the subject's health condition (e.g., worsening of heart failure or the like). In an embodiment, a corresponding weight can be applied to each of the point described above (e.g., each point is multiplied by the corresponding weight) to get a corresponding final point for the corresponding cardiopulmonary parameter (or the corresponding parameter change). Each weight applied for each of the point described above can be different from (or be the same as) other weight(s). In an embodiment, each weight can range from zero to one (or 100%). In another embodiment, each weight can range from zero to 10. In an embodiment, each weight can range from zero to 100. A total score can be determined by summing each of the corresponding final point up. For example, the total score can be A×sound change point(s)+B×heart rate change point(s)+C×thoracic impedance change point(s)+D×respiratory rate change point(s)+E×QRS wavelength change point(s)+F×QT interval change point(s)+G×electromechanical activation time change point(s)+H×left ventricular systolic time change point(s), where A-H can be the corresponding weights. In another embodiment, the total score can be determined by summing one or more of the corresponding final point up.

The method 300 proceeds to 340. At 340, the controller is configured to control an operation of the cardiopulmonary management system based on e.g., the determined total score. For example, when the total score is greater than a threshold (e.g., at or about 20 points or any suitable threshold), the controller is configured to send the corresponding data (e.g., all the data that corresponding to the total score, or all the data collected or sensed or measured) to a system (e.g., a system used by the subject's physician or the like), to generate an alarm (to the subject or to the physician), to take a corresponding action, or the like. The physician can decide whether to adjust the medication, whether to have the subject to see the physician, or the like, and take corresponding action(s), based on the data.

In an embodiment, the controller can be configured to generate an alarm on or evaluate the cardiopulmonary conditions such as a stable or instable heart condition (e.g., based on all of the measured thoracic impedance, electrocardiogram, and sounds data, or the like), a level of thoracic fluid content (e.g., based on the measured thoracic impedance data, or the like), heart failure (e.g., based on the measured electrocardiogram and sounds data, or the like), etc. based on the measured thoracic impedance, electrocardiogram, and/or sounds data.

Figure 6B:
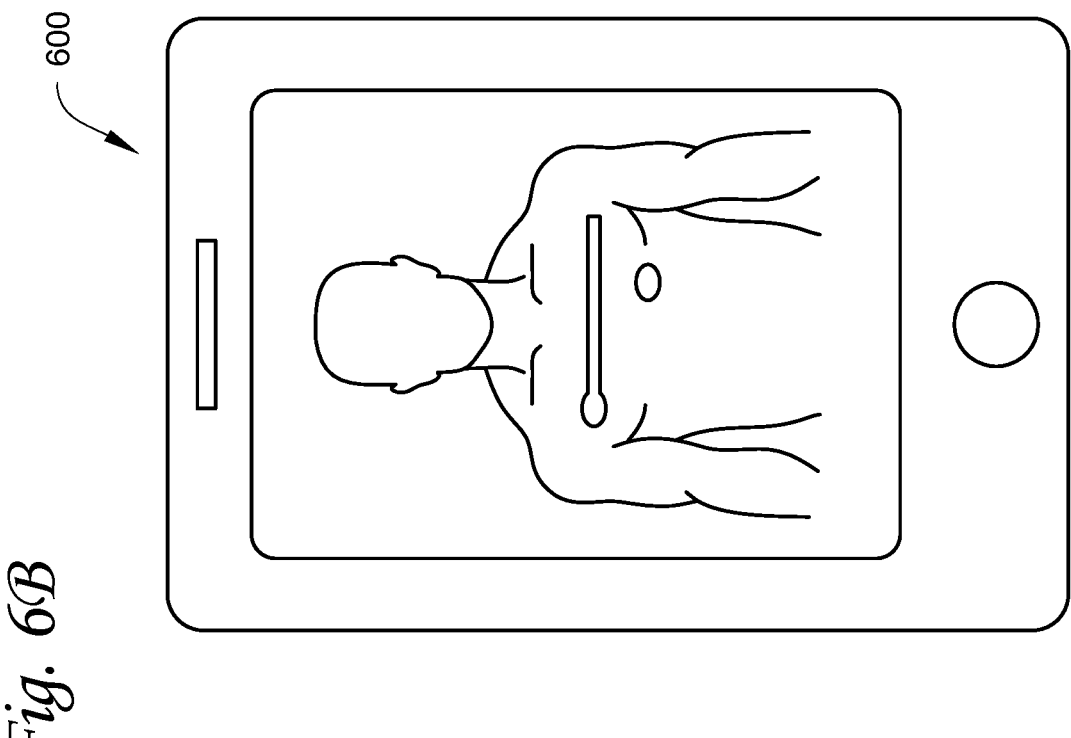
FIG. 6B illustrates a front view of a display device, according to an embodiment.
Figure 6A:
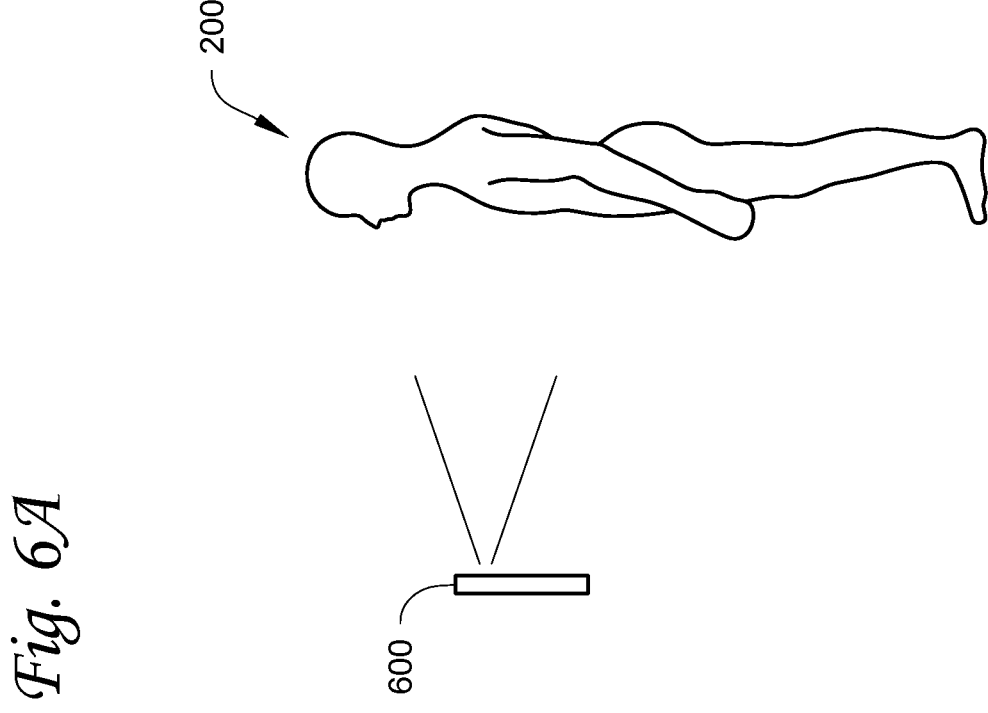
FIG. 6A illustrates a side view of capturing an image of a subject, according to an embodiment.

FIG. 6A illustrates a side view of a device 600 capturing an image (or video) of a subject 200, according to an embodiment. FIG. 6B illustrates a front view of a display device 600 with a graphic user interface (GUI), according to an embodiment.

As shown in FIG. 6A, the device 600 can be configured to capture an image (or video) of the subject 200. In an embodiment, the device 600 can be a camera, a video recorder, or any suitable device having image and/or video capturing capacity. As shown in FIG. 6B, the device 600 can be configured to display the captured image (or video) of the subject on the GUI. In an embodiment, the device of FIG. 6B is the device of FIG. 6A. In another embodiment, the device of FIG. 6B is different from the device of FIG. 6A, and the device of FIG. 6B obtains and displays the image captured by the device of FIG. 6A.

Figure 6C:
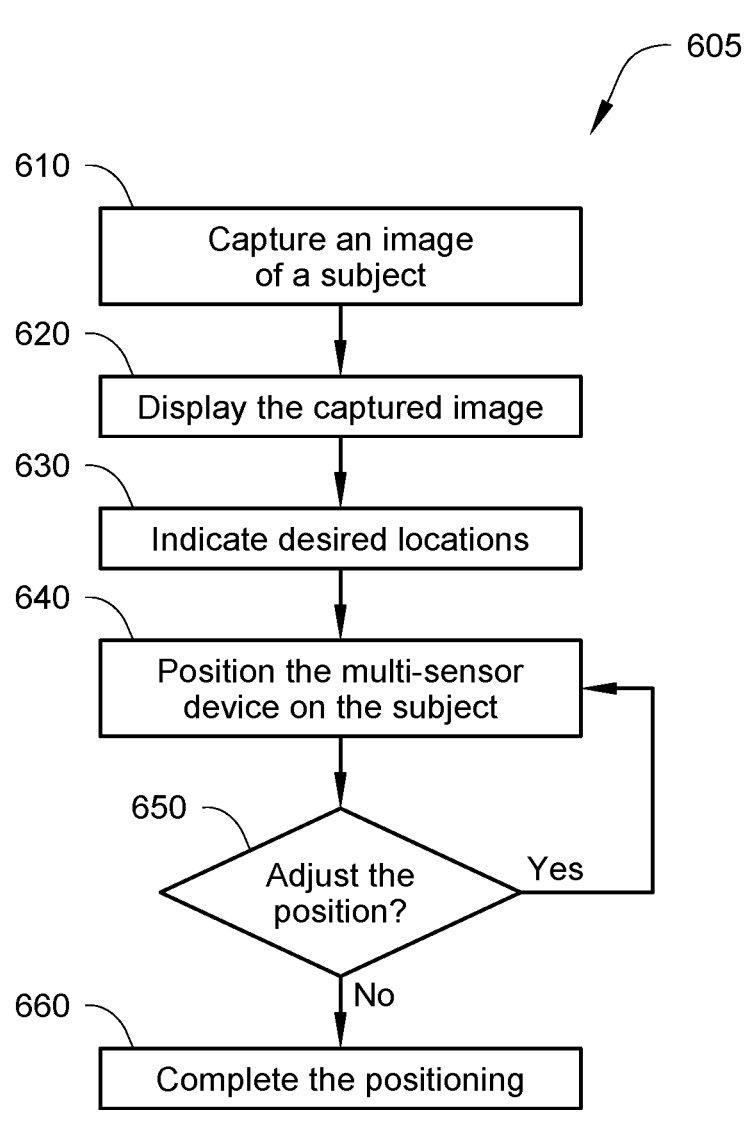
FIG. 6C is a flow chart illustrating a method of positioning a multi-sensor device, according to an embodiment.

FIG. 6C is a flow chart illustrating a method 605 of positioning a multi-sensor device (100 of FIG. 1 or 102 of FIG. 2) on a skin of a subject, according to an embodiment. It will be appreciated that the method steps disclosed herein can be conducted by a controller, unless otherwise specified. The controller can be the controller of the multi-sensor device, other controller (the controller of a portable or mobile electronic device, a specially programmed personal computer, a server, or controller(s) in the cloud, or the like), or the combination thereof. The controller can include a processor, memory, and/or communication ports to communicate with e.g., other components of the system, using any suitable communications including wired and/or wireless, analog and/or digital communications.

It will also be appreciated that the method 605 can include one or more operations, actions, or functions depicted by one or more blocks. Although illustrated as discrete blocks, various blocks may be divided into additional blocks, combined into fewer blocks, or eliminated, depending on the desired implementation. The method 605 can be in a form of e.g., an application for a mobile device, an algorithm, or the like.

The method 605 begins at 610. At 610, a user (e.g., the subject 200 of FIG. 3 or any other user) can capture, using the device 600 of FIG. 6A, an image (or video) of the subject.

The method 605 proceeds to 620. At 620, a display device (e.g. the device 600 of FIG. 6B or the like) can be configured to obtain and/or display the image captured at 610.

The method 605 proceeds to 630. At 630, a device (e.g., the device 600 of FIG. 6B or any other suitable device(s)) can be configured to analyze the captured and/or displayed image, to identify the desired locations for placing a multi-sensor device, and/or to indicate (e.g., via audio, video, marker(s) on the image, or the like) the desired locations on the captured or displayed image.

In an embodiment, the desired locations can include a first desired location for the first end of the elongated body of the multi-sensor device, a second desired location for the second end of the elongated body of the multi-sensor device, a third desired location for the sound sensor of the multi-sensor device, or the like.

The method 605 proceeds to 640. At 640, the user can position and/or secure the multi-sensor device on a skin of the subject. The user can e.g., position and/or secure the first end of the elongated body of the multi-sensor device at a first position corresponding to the first desired location on a skin of the subject, position and/or secure the second end of the elongated body of the multi-sensor device at a second position corresponding to the second desired location on the skin of the subject, and/or position and/or secure the sound sensor of the multi-sensor device at a third position corresponding to the third desired location on the skin of the subject.

It will be appreciated that the multi-sensor device can be secured on the skin of the subject by patch or pad, pressure, vacuum, or the like, or be secured by hand (e.g., by hand-holding the device against the skin).

In an embodiment, the user can position or span the elongated body of the multi-sensor device across a chest of the subject (e.g., by aligning the elongated body of the multi-sensor device with the collarbone of the subject). In such embodiment, the thoracic impedance measured can be the transthoracic impedance (measured cross the entire pair of lungs), which might be the desired thoracic impedance to be measured. The user can also align the extension (e.g., 150 of FIG. 1) with the navel of the subject so that the first position and the second position can be identified or determined.

In an embodiment, the user can position and/or secure the sound sensor on the skin of the subject near a cardiac apex, which is at or near the fifth intercostal space, for measuring heart sounds. In another embodiment, the user can position and/or secure the sound sensor on the skin at a back of the subject near a lung, for measuring lung sounds.

In an embodiment, the user can position and/or secure each of the electrodes of the multi-sensor device by positioning each pad between each electrode and the skin of the subject.

In an embodiment, the user can capture, using the device 600 of FIG. 6A, another image (or video) of the subject together with the positioned multi-sensor device.

The method 605 proceeds to 650. At 650, the device of 630 can determine whether the position(s) of the multi-sensor device need to be adjusted. When there is a mismatch between the first position and the first desired location, a mismatch between the second position and the second desired location, and/or a mismatch between the third position and the third desired location, an alarm (audio, video, marker(s) on the image, or the like) can be generated, and method 605 proceeds back to 640 (to e.g., adjust the first, second, and/or third position based on the alarm). In an embodiment, a mismatch between a position and the desired location can be referred to as that the position is not aligned with the desired location plus or minus a predetermined tolerance.

When there is no mismatch between the first position and the first desired location, between the second position and the second desired location, and/or between the third position and the third desired location, the method 605 proceeds to 660.

In another embodiment, at 650, the multi-sensor device can be configured to run a test, and can determine whether to proceed to 660 (if the testing measurement is greater than a threshold indicating a reliable measurement signal) or to 640 (if the testing measurement is not greater than the threshold indicating a not reliable measurement signal).

It will be appreciated that positioning the multi-sensor device at a same, fixed, desired location can be important since changing the location of the measurements might result in inconsistent measurements and might result in incorrect alarm of worsening health conditions.

At 660, the positioning is complete, and the user can start the multi-sensor device for sensing or measuring. In an embodiment, to best measure S3, the subject may be in a left lateral decubitus position. In an embodiment, to get a reliable measurement, the subject may rest in a quite environment (e.g., for at or about 10 minutes) before automatically (through a timer or the like) or manually (by pressing a start button or the like) starting the multi-sensor device. The multi-sensor device can run e.g., for at or about 15 seconds to measure the cardiopulmonary parameters. In an embodiment, the subject can position and run or start the multi-sensor device before sleeping or going to bed, and stop and/or take off the multi-sensor device when waking up.

Figure 7:
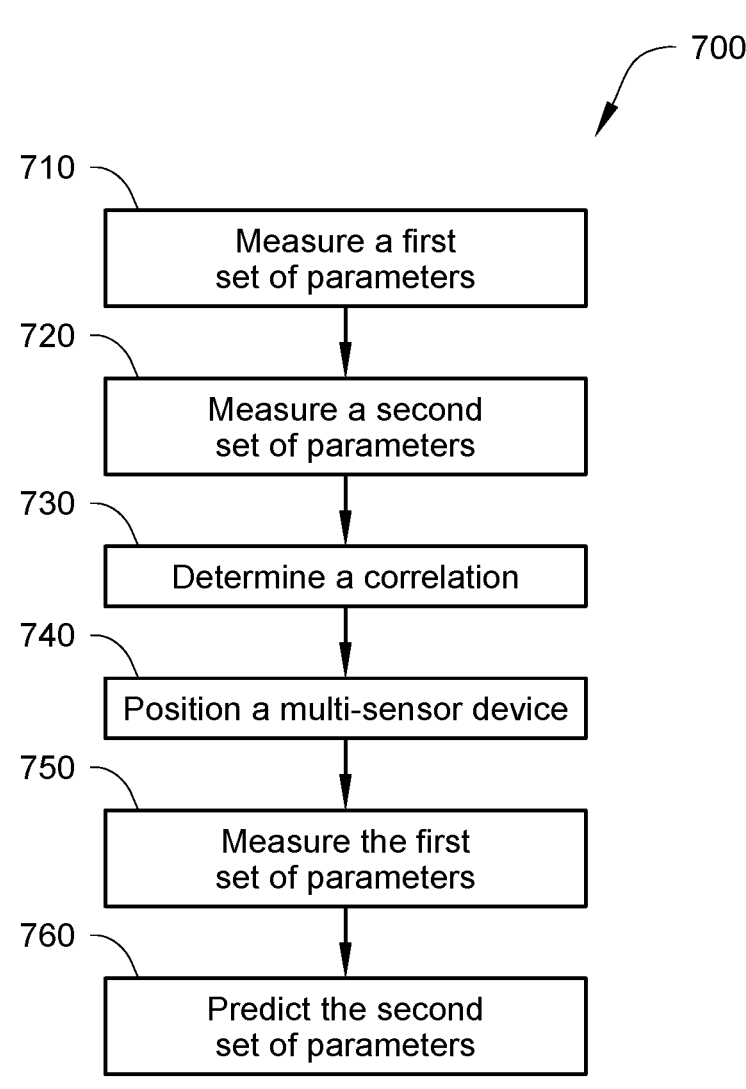
FIG. 7 is a flow chart illustrating a method of predicting and/or estimating cardiopulmonary parameters, according to an embodiment.

FIG. 7 is a flow chart illustrating a method 700 of predicting and/or estimating cardiopulmonary parameters using a machine learning system, according to an embodiment. It will be appreciated that the method steps disclosed herein can be conducted by a controller, unless otherwise specified. The controller can be the controller of the multi-sensor device, other controller (the controller of a portable/mobile electronic device, a specially programmed personal computer, a server, or controller(s) in the cloud, or the like), or the combination thereof.

The controller can include a processor, memory, and/or communication ports to communicate with e.g., other components of the system, using any suitable communications including wired and/or wireless, analog and/or digital communications. The controller can obtain data sensed or measured by the sensors and/or electrodes and control the settings of the sensors and/or electrodes and/or other components of the system.

It will also be appreciated that the method 700 can include one or more operations, actions, or functions depicted by one or more blocks. Although illustrated as discrete blocks, various blocks may be divided into additional blocks, combined into fewer blocks, or eliminated, depending on the desired implementation. The method 700 can deploy e.g., a trained machine learning model (e.g., a cardiopulmonary parameters model, or the like) to determine cardiopulmonary parameters based on a different set of cardiopulmonary parameters using machine learning technologies. The method 700 can be in a form of e.g., an application for a mobile device, an algorithm, or the like.

The method 700 begins at 710. At 710, the controller is configured to determine or obtain a first set of cardiopulmonary parameters from one or more subjects. The first set of cardiopulmonary parameters can include left ventricular ejection fraction (LVEF), B-type natriuretic peptide (BNP), or the like.

LVEF is a measurement of how much blood is being pumped out of the LV of the heart with each contraction, and can be represented as a fraction of chamber volume ejected in systole (stroke volume) in relation to the volume of the blood in the LV at the end of diastole (end-diastolic volume). In an embodiment, LVEF can be measured or determined by conducting echocardiography and the corresponding analysis.

BNP is a hormone produced by the heart, which can also be used as a bio-marker for heart failure and/or heart tissue damage. In an embodiment, BNP can be measured or determined by conducting blood testing and the corresponding analysis.

The measured or determined first set of cardiopulmonary parameters can be obtained by the controller. The method 700 proceeds to 720.

At 720, the controller is configured to determine or obtain a second set of cardiopulmonary parameters from the one or more subjects from 710. It will be appreciated that the second set of cardiopulmonary parameters may be measured or determined at or around the same time as the first set of cardiopulmonary parameters.

The second set of cardiopulmonary parameters can include thoracic (or transthoracic) impedance, electrocardiogram of the heart, sounds (heart sound, lung sounds, etc.), or the like. The second set of cardiopulmonary parameters may be measured or determined using the method step 320 of FIG. 5 or any other suitable means. The determined set of cardiopulmonary parameters can be obtained by the controller.

The method 700 proceeds to 730. At 730, a correlation between the measured or determined first set of cardiopulmonary parameters and the measured or determined second set of cardiopulmonary parameters can be determined, e.g., using machine learning or any other suitable means.

For example, the determined first and second sets of cardiopulmonary parameters can be used as input to a cardiopulmonary parameters model. A correlation between the first set of cardiopulmonary parameters and the second set of cardiopulmonary parameters can be determined by e.g., training the cardiopulmonary parameters model (e.g., by the controller). The running of the trained cardiopulmonary parameters model (e.g., by the controller) can provide outputs such as the predicted LVEF, the predicted BNP, or the like.

It will be appreciated that at 730, the controller can be configured to create the machine learning model (e.g., the cardiopulmonary parameters model, or the like). The machine learning model can be saved in e.g., a memory or any other suitable devices. It will be appreciated that the controller can be configured to train the machine learning model using data from 710 and 720. It will be appreciated that the controller can be configured to deploy the trained machine learning model for use. For example, the trained machine learning model can be deployed to a controller in the field for use. It will be appreciated that the type and/or source of the data for running the trained machine learning model can be similar to the type and/or source of the data for training the machine learning model. It will be appreciated that the controller can be configured to re-train the machine learning model using updated or new training data. It will also be appreciated that neural network such as convolutional neural network or the like can be used as a tool for the machine learning process.

It will also be appreciated that preferably, personalized machine learning model (e.g., cardiopulmonary parameters data collected for a particular subject) may be used to predict cardiopulmonary parameters for that particular subject to provide more accuracy. It will further be appreciated that cardiopulmonary parameters data collected from other subjects may also be used to predict cardiopulmonary parameters for a subject.

The method 700 proceeds to 740. At 740, a multi-sensor device can be positioned on a skin of a subject. In an embodiment, the method step 740 is similar to or the same as the method steps described in FIG. 6C.

The method 700 proceeds to 750. At 750, the multi-sensor device is configured to run, and cardiopulmonary parameters (e.g., thoracic impedance, electrocardiogram, sounds, or the like.) can be sensed or measured from the subject. In an embodiment, the measuring step in 750 is similar to or the same as the method step 320 described in FIG. 5.

The method 700 proceeds to 760. At 760, the controller is configured to predict the second set of parameters (LVEF, BNP, or the like) for the subject based on the cardiopulmonary parameters measured for the subject at 750 (and/or the correlation determined at 730) by e.g., running the trained cardiopulmonary parameters model at 730 using the cardiopulmonary parameters measured at 750 as input data.

Embodiments disclosed herein can provide a low cost, easy to use and easy to remove, and low risk (e.g., of trauma or infection or the like) system and/or device compared with an implantable device. Embodiments disclosed herein can provide a system and/or device that uses one or more or all of the measured thoracic impedance, electrocardiogram, and sounds. Embodiments disclosed herein can further provide an alarm of acute worsening of heart failure with high sensitivity (e.g., at or about or above 70%) and/or plentiful advance (e.g., at or about or more than 34 days before the acute worsening of heart failure occurs).

ASPECTS

It is appreciated that any one of aspects can be combined with other aspect(s).

Aspect 1. A cardiopulmonary management system, comprising:
a multi-sensor device; and
a controller,
wherein the multi-sensor device includes an elongated body having a first end and a second end, a first electrode disposed at the first end of the body, a second electrode disposed at the second end of the body, an electrical circuitry disposed near a middle of the body, and a sound sensor,
the multi-sensor device is configured to be disposed on a skin of a subject and to measure cardiopulmonary parameters from the subject, the controller is configured to derive a score of sound change, heart rate change, thoracic impedance change, respiratory rate change, QRS wavelength change, QT interval change, electromechanical activation time change, and left ventricular systolic time change based on the measured cardiopulmonary parameters,
the controller is further configured to control an operation of the system when the derived score is greater than a threshold.

Aspect 2. The system according to aspect 1, wherein the elongated body of the multi-sensor device spans across a chest of the subject.

Aspect 3. The system according to aspect 1 or aspect 2, wherein the cardiopulmonary parameters include thoracic impedance, electrocardiogram, and heart sounds.

Aspect 4. The system according to aspect 3, wherein the first electrode and the second electrode are configured to measure the thoracic impedance and the electrocardiogram, the sound sensor is configured to measure the heart sounds.

Aspect 5. The system according to aspect 3 or aspect 4, wherein the sound sensor is disposed on the skin of the subject near a cardiac apex.

Aspect 6. The system according to any one of aspects 3-5, wherein the sound change is a change of a ratio of an intensity of a third heart sound (S3) to an intensity of a first heart sound (S1) when the S3 is detected by the sound sensor.

Aspect 7. The system according to aspect 1 or aspect 2, wherein the sound sensor is disposed at a back of the subject near a lung.

Aspect 8. The system according to aspect 7, wherein the sound sensor is configured to measure lung sounds.

Aspect 9. The system according to any one of aspects 1-8, wherein the heart rate change is a change of heart rate based on a heart rate baseline.

Aspect 10. The system according to any one of aspects 1-9, wherein the thoracic impedance change is a change of thoracic impedance based on a thoracic impedance baseline.

Aspect 11. The system according to any one of aspects 1-10, wherein the respiratory rate change is a change of respiratory rate based on a respiratory rate baseline.

Aspect 12. The system according to any one of aspects 1-11, wherein the QRS wavelength change is a change of QRS wavelength based on a QRS wavelength baseline.

Aspect 13. The system according to any one of aspects 1-12, wherein the QT interval change is a change of QT interval based on a QT interval baseline.

Aspect 14. The system according to any one of aspects 1-13, wherein the electromechanical activation time change is a change of electromechanical activation time based on an electromechanical activation time baseline.

Aspect 15. The system according to any one of aspects 1-14, wherein the left ventricular systolic time change is a change of left ventricular systolic time based on a left ventricular systolic time baseline.

Aspect 16. The system according to any one of aspects 1-15, wherein the multi-sensor device further includes an extension extending cross the middle of the elongated body, the extension has a first end and a second end, the sound sensor is disposed at the second end of the extension.

Aspect 17. The system according to aspect 16, wherein the multi-sensor device further includes a contact charging point disposed at the first end of the extension.

Aspect 18. The system according to any one of aspects 1-17, wherein the multi-sensor device further includes a third electrode disposed at the first end of the body, and a fourth electrode disposed at the second end of the body.

Aspect 19. The system according to any one of aspects 1-18, further comprising a first pad disposed between the first electrode and the skin of the subject, and a second pad disposed between the second electrode and the skin of the subject.

Aspect 20. The system according to any one of aspects 1-19, wherein the multi-sensor device further includes a contact charging point disposed on the electrical circuitry.

Aspect 21. The system according to any one of aspects 1-20, wherein the multi-sensor device further includes an extension separate from the body of the multi-sensor device, the sound sensor is disposed on the extension.

Aspect 22. The system according to aspect 21, wherein the extension has a first end and a second end, a first extension electrode is disposed at the first end of the extension, a second extension electrode is disposed at the second end of the extension, and the sound sensor is disposed near a middle of the extension.

Aspect 23. The system according to aspect 22, wherein the extension further includes a contact charging point disposed at the first end of the extension.

Aspect 24. A method of controlling an operation of a cardiopulmonary management system, the system including a multi-sensor device and a controller; the multi-sensor device including an elongated body having a first end and a second end, a first electrode disposed at the first end of the body, a second electrode disposed at the second end of the body, an electrical circuitry disposed near a middle of the body, and a sound sensor; the method comprising:

positioning the multi-sensor device on a skin of a subject;

sensing cardiopulmonary parameters from the subject;

deriving a score of sound change, heart rate change, thoracic impedance change, respiratory rate change, QRS wavelength change, QT interval change, electromechanical activation time change, and left ventricular systolic time change based on the measured cardiopulmonary parameters;

controlling the operation of the system when the derived score is greater than a threshold.

Aspect 25. The method according to aspect 24, further comprising:

spanning the elongated body of the multi-sensor device across a chest of the subject.

Aspect 26. The method according to aspect 24 or aspect 25, wherein the cardiopulmonary parameters include thoracic impedance, electrocardiogram, and heart sounds.

Aspect 27. The method according to aspect 26, further comprising:

determining the thoracic impedance and the electrocardiogram by the first electrode and the second electrode, and sensing the heart sounds by the sound sensor.

Aspect 28. The method according to aspect 26 or aspect 27, further comprising:

positioning the sound sensor on the skin of the subject near a cardiac apex.

Aspect 29. The method according to any one of aspects 26-28, wherein the sound change is a change of a ratio of an intensity of a third heart sound (S3) to an intensity of a first heart sound (S1) when the S3 is detected by the sound sensor.

Aspect 30. The method according to aspect 24 or aspect 25, further comprising:

positioning the sound sensor at a back of the subject near a lung.

Aspect 31. The method according to aspect 30, further comprising:

sensing lung sounds by the sound sensor.

Aspect 32. The method according to any one of aspects 24-31, wherein the heart rate change is a change of heart rate based on a heart rate baseline.

Aspect 33. The method according to any one of aspects 24-32, wherein the thoracic impedance change is a change of thoracic impedance based on a thoracic impedance baseline.

Aspect 34. The method according to any one of aspects 24-33, wherein the respiratory rate change is a change of respiratory rate based on a respiratory rate baseline.

Aspect 35. The method according to any one of aspects 24-34, wherein the QRS wavelength change is a change of QRS wavelength based on a QRS wavelength baseline.

Aspect 36. The method according to any one of aspects 24-35, wherein the QT interval change is a change of QT interval based on a QT interval baseline.

Aspect 37. The method according to any one of aspects 24-36, wherein the electromechanical activation time change is a change of electromechanical activation time based on an electromechanical activation time baseline.

Aspect 38. The method according to any one of aspects 24-37, wherein the left ventricular systolic time change is a change of left ventricular systolic time based on a left ventricular systolic time baseline.

Aspect 39. The method according to any one of aspects 24-38, wherein the multi-sensor device further includes an extension extending cross the middle of the elongated body, the extension has a first end and a second end, the sound sensor is disposed at the second end of the extension.

Aspect 40. The method according to aspect 39, wherein the multi-sensor device further includes a contact charging point disposed at the first end of the extension.

Aspect 41. The method according to any one of aspects 24-40, wherein the multi-sensor device further includes a third electrode disposed at the first end of the body, and a fourth electrode disposed at the second end of the body.

Aspect 42. The method according to any one of aspects 24-41, further comprising:

positioning a first pad between the first electrode and the skin of the subject; and positioning a second pad between the second electrode and the skin of the subject.

Aspect 43. The method according to any one of aspects 24-42, wherein the multi-sensor device further includes a contact charging point disposed on the electrical circuitry.

Aspect 44. The method according to any one of aspects 24-43, wherein the multi-sensor device further includes an extension separate from the body of the multi-sensor device, the sound sensor is disposed on the extension.

Aspect 45. The method according to aspect 44, wherein the extension has a first end and a second end, a first extension electrode is disposed at the first end of the extension, a second extension electrode is disposed at the second end of the extension, and the sound sensor is disposed near a middle of the extension.

Aspect 46. The method according to aspect 45, wherein the extension further includes a contact charging point disposed at the first end of the extension.

Aspect 47. A method of predicting cardiopulmonary parameters, the method comprising:

measuring a first set of cardiopulmonary parameters;

measuring a second set of cardiopulmonary parameters;

determining a correlation between the first set of cardiopulmonary parameters and the second set of cardiopulmonary parameters using machine learning;

positioning a multi-sensor device on a skin of a subject;

sensing the first set of cardiopulmonary parameters from the subject by the multi-sensor device;

predicting the second set of cardiopulmonary parameters for the subject based on the determined correlation using machine learning.

Aspect 48. The method according to aspect 47, wherein the first set of cardiopulmonary parameters include thoracic impedance, electrocardiogram, and heart sounds.

Aspect 49. The method according to aspect 47 or aspect 48, wherein the second set of cardiopulmonary parameters include left ventricular ejection fraction and B-type natriuretic peptide.

Aspect 50. A method of positioning a multi-sensor device, the multi-sensor device including an elongated body having a first end and a second end, a first electrode disposed at the first end of the body, a second electrode disposed at the second end of the body, and a sound sensor, the method comprising:

capturing, by a camera, an image of a subject;

displaying the captured image on a display device;

indicating a first location, a second location, and a third location on the displayed image;

positioning and securing the first end of the elongated body of the multi-sensor device at a first position corresponding to the first location on a skin of the subject;

positioning and securing the second end of the elongated body of the multi-sensor device at a second position corresponding to the second location on the skin of the subject; and positioning and securing the sound sensor at a third position corresponding to the third location on the skin of the subject.

Aspect 51. The method according to aspect 50, further comprising:

capturing a second image of the subject with the multi-sensor device;

generating an alarm indicating a mismatch between the first position and the first location, a mismatch between the second position and the second location, or a mismatch between the third position and the third location; and adjusting the first position, the second position, or the third position based on the alarm.

Aspect 52. The method according to aspect 50 or aspect 51, further comprising:

positioning a first pad between the first electrode and the skin of the subject; and positioning a second pad between the second electrode and the skin of the subject.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This specification and the embodiments described are exemplary only, with the true scope and spirit of the disclosure being indicated by the claims that follow.

What is claimed is:

1. A cardiopulmonary management system, comprising:

a multi-sensor device; and a controller, wherein the multi-sensor device includes an elongated body having a first end and a second end, a first electrode disposed at the first end of the elongated body, a second electrode disposed at the second end of the elongated body, an electrical circuitry including the controller disposed near a middle of the elongated body, and a sound sensor, the multi-sensor device is configured to be disposed on a skin of a subject and to measure cardiopulmonary parameters from the subject, the controller is configured to derive a score of sound change, heart rate change, thoracic impedance change, respiratory rate change, QRS wavelength change, QT interval change, electromechanical activation time change, and left ventricular systolic time change based on the measured cardiopulmonary parameters, the controller is further configured to control an operation of the system when the derived score is greater than a threshold, the elongated body of the multi-sensor device is adapted to extend in a horizontal direction from one armpit to another armpit across an entire chest of the subject the sound sensor is spaced from the elongated body in a vertical direction, the system further comprises an extension extending across the middle of the elongated body, wherein the extension has a first end and a second end, the first end and the second end of the extension are on opposite sides of the elongated body in the vertical direction such that the first end of the extension is above the elongated body and the second end of the extension is below the elongated body, the sound sensor is disposed at the second end of the extension, and a contact charging point is disposed at the first end of the extension.

2. The system according to claim 1, wherein the cardiopulmonary parameters include thoracic impedance, electrocardiogram, and heart sounds.

3. The system according to claim 2, wherein the sound sensor is adapted to be disposed on the skin of the subject near a cardiac apex and is configured to measure the heart sounds.

4. The system according to claim 1, wherein the sound change is a change of a ratio of an intensity of a third heart sound (S3) to an intensity of a first heart sound (S1) when the S3 is detected by the sound sensor.

5. The system according to claim 1, wherein the multi-sensor device further includes a third electrode disposed at the first end of the elongated body, and a fourth electrode disposed at the second end of the elongated body.

6. The system according to claim 5, wherein the first electrode and the second electrode are aligned with each other in a substantially horizontal direction, the third electrode and the fourth electrode are aligned with each other in a substantially horizontal direction, a distance between the first electrode and the third electrode ranges from at or about two centimeters to at or about four centimeters.

7. A method of controlling an operation of a cardiopulmonary management system, the system including a multi-sensor device and a controller; the multi-sensor device including an elongated body having a first end and a second end, a first electrode disposed at the first end of the elongated body, a second electrode disposed at the second end of the elongated body, an electrical circuitry including the controller disposed near a middle of the elongated body, and a sound sensor; the method comprising:

positioning the multi-sensor device on a skin of a subject;

spanning the elongated body of the multi-sensor device across a chest of the subject;

sensing cardiopulmonary parameters from the subject;

deriving a score of sound change, heart rate change, thoracic impedance change, respiratory rate change, QRS wavelength change, QT interval change, electromechanical activation time change, and left ventricular systolic time change based on the measured cardiopulmonary parameters; and controlling the operation of the system when the derived score is greater than a threshold, wherein the elongated body of the multi-sensor device extends in a horizontal direction from one armpit to another armpit across an entire chest of the subject, the sound sensor is spaced from the elongated body in a vertical direction, the system further comprises an extension extending across the middle of the elongated body, wherein the extension has a first end and a second end, the first end and the second end of the extension are on opposite sides of the elongated body in the vertical direction such that the first end of the extension is above the elongated body and the second end of the extension is below the elongated body, the sound sensor is disposed at the second end of the extension, and a contact charging point is disposed at the first end of the extension.

8. The method according to claim 7, wherein the cardiopulmonary parameters include thoracic impedance, electrocardiogram, and heart sounds.

9. The method according to claim 8, further comprising:

positioning the sound sensor on the skin of the subject near a cardiac apex, and sensing the heart sounds by the sound sensor.

10. The method according to claim 7, wherein the sound change is a change of a ratio of an intensity of a third heart sound (S3) to an intensity of a first heart sound (S1) when the S3 is detected by the sound sensor.

11. The method according to claim 7, wherein the multi-sensor device further includes a third electrode disposed at the first end of the elongated body, and a fourth electrode disposed at the second end of the elongated body.

12. The method according to claim 11, wherein the first electrode and the second electrode are aligned with each other in a substantially horizontal direction, the third electrode and the fourth electrode are aligned with each other in a substantially horizontal direction, a distance between the first electrode and the third electrode ranges from at or about two centimeters to at or about four centimeters.

13. The method according to claim 7, further comprising:

positioning a first pad between the first electrode and the skin of the subject in a direction perpendicular to the horizontal direction and the vertical direction; and positioning a second pad between the second electrode and the skin of the subject in the direction perpendicular to the horizontal direction and the vertical direction.

14. The method according to claim 7, further comprising:

capturing, by a camera, an image of the subject;

displaying the captured image on a display device;

indicating a first location, a second location, and a third location on the displayed image;

positioning and securing the first end of the elongated body of the multi-sensor device at a first position corresponding to the first location on the skin of the subject;

positioning and securing the second end of the elongated body of the multi-sensor device at a second position corresponding to the second location on the skin of the subject; and positioning and securing the sound sensor at a third position corresponding to the third location on the skin of the subject.

15. The method according to claim 14, further comprising:

capturing a second image of the subject with the multi-sensor device;

generating an alarm indicating a mismatch between the first position and the first location, a mismatch between the second position and the second location, or a mismatch between the third position and the third location; and adjusting the first position, the second position, or the third position based on the alarm.

16. The system according to claim 1, wherein the elongated body is made of flexible silicone such that a length of the elongated body is extendable and retractable.

17. The system according to claim 1, wherein the first electrode and the second electrode are configured to measure thoracic impedance and electrocardiogram.

18. The system according to claim 1, further comprising a first pad is adapted to be disposed between the first electrode and the skin of the subject in a direction perpendicular to the horizontal direction and the vertical direction, and a second pad is adapted to be disposed between the second electrode and the skin of the subject in the direction perpendicular to the horizontal direction and the vertical direction.

19. The system according to claim 1, wherein the multi-sensor device includes a first wire extending horizontally along the elongated body to reach the electrical circuitry including the controller, and a second wire extending horizontally along the elongated body to reach the electrical circuitry including the controller.

20. The system according to claim 1, wherein the electrical circuitry including the controller covers opposite sides of the elongated body in the vertical direction and covers opposite sides of the extension in the horizontal direction in a plan view.

* * * * *